United States Patent [19]
Kesling

[11] Patent Number: 6,024,564
[45] Date of Patent: Feb. 15, 2000

[54] ROTATING PERIODONTAL PROBE

[76] Inventor: Peter C. Kesling, 611 W. 250 South, LaPorte, Ind. 46350

[21] Appl. No.: 09/336,293

[22] Filed: Jun. 21, 1999

[51] Int. Cl.⁷ .................................................. A61C 19/04
[52] U.S. Cl. ............................................. 433/72; 433/141
[58] Field of Search ................................ 433/72, 75, 141, 433/142, 143, 144

[56] References Cited

U.S. PATENT DOCUMENTS

| | | | |
|---|---|---|---|
| 5,188,617 | 2/1993 | Linder | 433/72 X |
| 5,271,734 | 12/1993 | Takeuchi | 433/72 |
| 5,486,109 | 1/1996 | Hunter et al. | 433/72 |
| 5,587,284 | 12/1996 | Brattesani | 433/72 |
| 5,676,544 | 10/1997 | Urban | 433/72 X |
| 5,725,373 | 3/1998 | Yeh | 433/72 |

*Primary Examiner*—Nicholas D. Lucchesi
*Attorney, Agent, or Firm*—Lloyd L. Zickert

[57] ABSTRACT

A periodontal probe having blade-shaped head for use in measuring the depth of gingival pockets of a patient's teeth more comfortably and accurately.

27 Claims, 4 Drawing Sheets

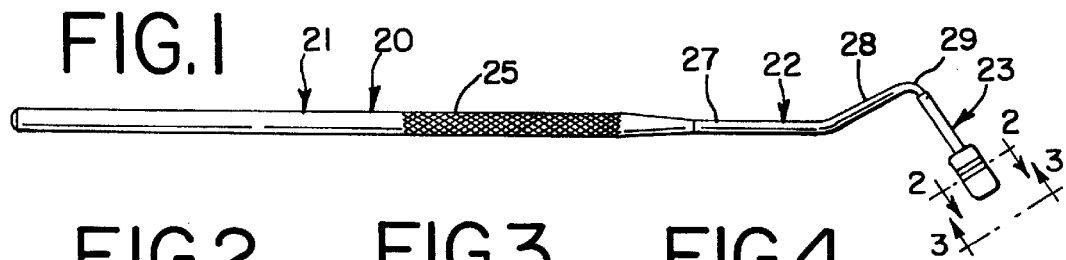
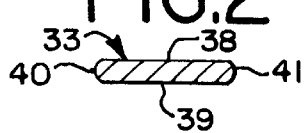 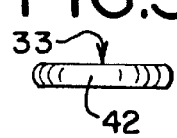 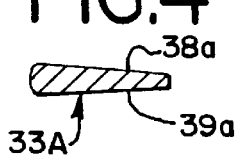
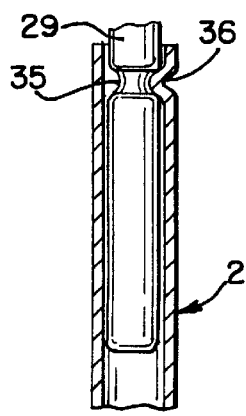
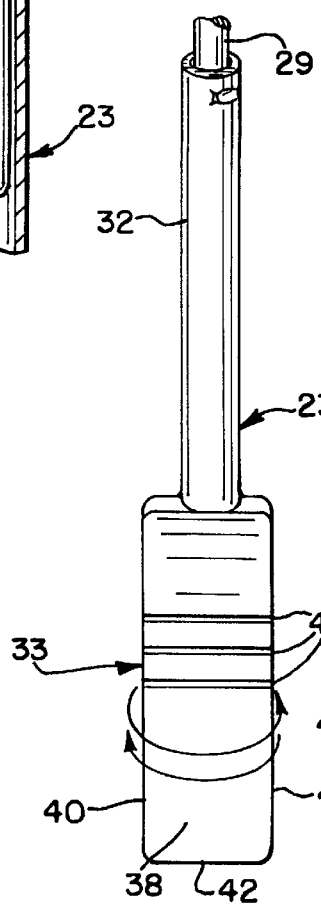
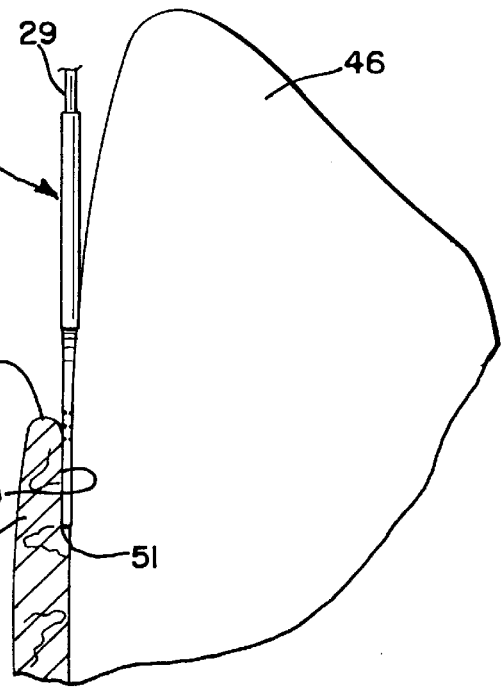

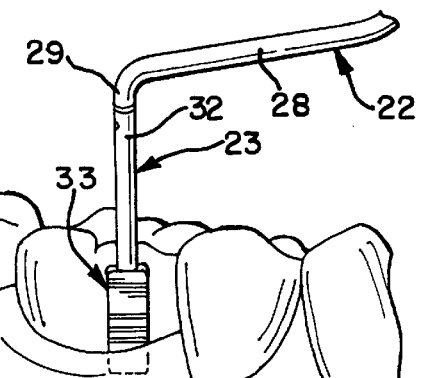
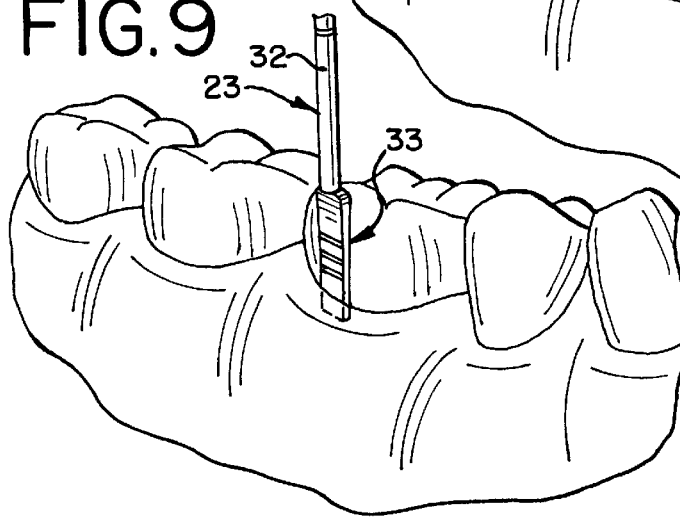
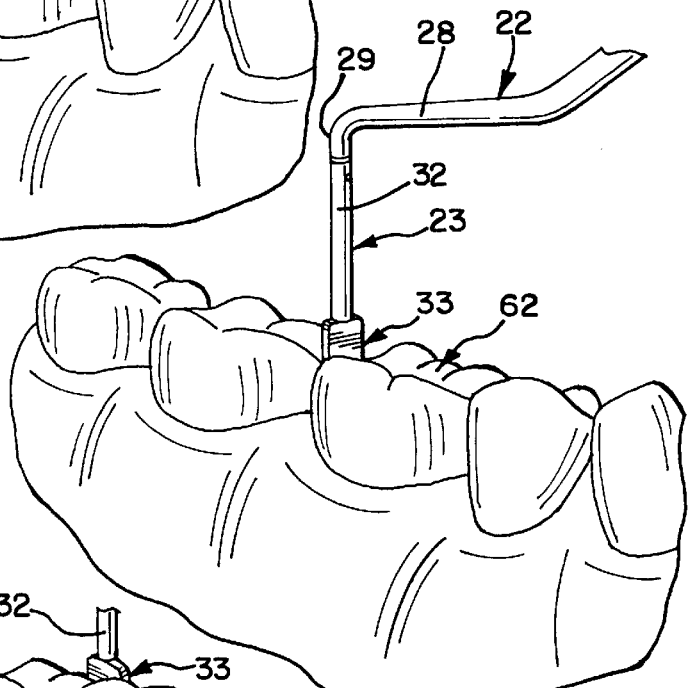
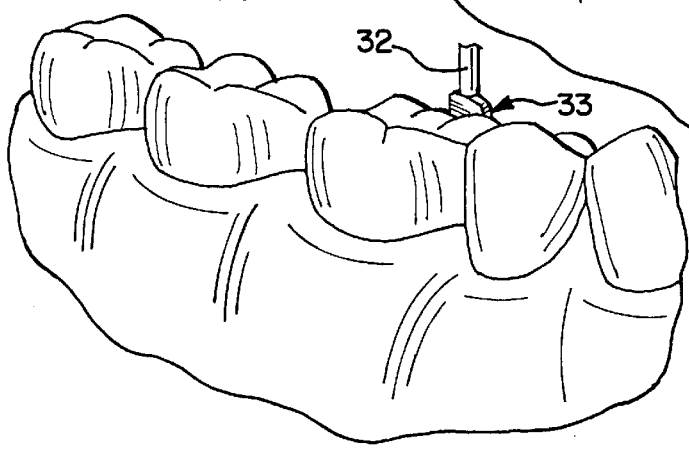

ROTATING PERIODONTAL PROBE

DESCRIPTION

This invention relates in general to a periodontal probe for measuring the gingival pockets or sulcus of a patient's teeth, and more particularly to a periodontal probe having a relatively thin rotating head that is provided with a broad or blunt end for insertion into the gingival sulcus to measure the depth of the sulcus.

BACKGROUND OF THE INVENTION

During the examination of a patient's teeth, a dentist will examine the health of the gums or gingiva, and more particularly, manipulate an instrument for measuring the depths of the gingival pockets or sulcii around the teeth. This procedure usually takes place during the cleaning of the teeth.

Heretofore, a periodontal probe used for measuring the gingival pocket depth consisted of a handle having a head angularly related to the handle. The head was in the form of a cylindrical pin that is relatively small in diameter, approximately 0.15 inches, so that the head can easily slip between the tooth surface and the free gum margin to determine the depth of the gingival pocket. Such a probe, being relatively small in diameter, when inserted to the bottom of the pocket or sulcus, can be uncomfortable, much like a pin prick each time the bottom is touched. In fact, it would be possible for the dentist to inadvertently penetrate and puncture the periodontal fibers at the bottom of the sulcus which, while being painful, adds the problem of potentially allowing bacteria into the patient's bloodstream.

The periodontal probe of the present invention overcomes these problems by providing a probe that is simple to use, provides comfort to the patient, and substantially avoids the danger of puncturing the periodontal fibers.

SUMMARY OF THE INVENTION

The periodontal probe of the present invention includes a flat, rotatable head mounted on the end of a handle. The rotating head of the probe is inserted into the gingival sulcus to measure the sulcus depth at the point of insertion, withdrawn from the sulcus, and then can be manipulated to traverse the tooth surface and rotate to be inserted and determine the depths of the sulcus on all sides. Slight pressure against the tooth causes the head to rotate as the probe is traversed around the tooth. This ensures that the thin dimension of the head is always parallel with the gingival sulcus as it follows the contour of the tooth. At desired locations, the probe can be moved apically of the tooth to determine the depth of the sulcus.

The head of the probe is generally in the form a blade where the broad sides may be parallel or non-parallel to each other while defining an end that has a relatively narrow, substantially linear or broad surface for engaging the bottom of the gingival sulcus. The head is usually angularly mounted on the handle to facilitate the insertion into the mouth by a dentist or a dental hygienist.

The head may take a number of forms as long as it provides a blade-like shape which may be substantially square, rectangular, triangular, oval, or circular in form. Additionally, the head may be made of plastic or other suitable material and removable from the handle for purposes of facilitating the autoclavability of the instrument. When removable the head may be disposable if desired. Thus, if disposable, the head may be made of a suitable plastic material wherein the end of the handle and head would have a suitable connecting means to not only maintain the head on the handle during use but also to allow it to rotate relative to the handle to facilitate its use.

Thus, the head of the probe would be freely rotatable and provide a relatively flat surface to not only assist in guiding the head around a tooth but also in defining a relatively blunt end that would be comfortable to the patient during its use.

It is therefore an object of the present invention to provide a new and improved periodontal probe for use on a dental patient to measure the depths of the gingival sulcii or pockets and which is comfortable to the patient during the measuring procedure.

A further object of the present invention is in the provision of a periodontal probe having a rotating head in the form of blade or paddle that can rotate on the handle of the probe during the procedure for measuring the depth of the gingival sulcus around a tooth.

A further object of the present invention is in the provision of a periodontal probe having a rotating head with a blunt end and which is broad enough in one dimension to substantially eliminate the puncturing of the periodontal fibers during the measuring of the depth of the sulcus and narrow enough in the other dimension to slip comfortably between the gingiva and the tooth.

A further object of the present invention is in the provision of a periodontal probe having a removable blade or paddle-shaped head that may be disposable and which would enhance the autoclavability of the handle.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is an elevational view of a periodontal probe according to the invention and having a rotatable head;

FIG. 2 is an enlarged transverse sectional view taken through the end of the head of the probe in FIG. 1 and substantially along line 2—2 of FIG. 1;

FIG. 3 is an enlarged end view of the probe head in FIG. 1 and looking in the direction of the arrows 3—3 in FIG. 1;

FIG. 4 is a transverse sectional view taken through a modified head for a probe of the present invention and showing the sides tapered;

FIG. 5 is a fragmentary greatly enlarged sectional view taken axially through the connecting portion of the head and showing how the head on the probe is maintained in attached rotatable relation to the handle;

FIG. 6 is an enlarged elevational view of the head of the embodiment of FIG. 1;

FIG. 7 is an end elevational view of the head of the probe in FIG. 1 and as it is being inserted in the gingival sulcus or pocket of a tooth and illustrating the tooth and gingiva for receiving the head of the probe;

FIGS. 8, 9, 10 and 11 are perspective views of the end of a probe according to the present invention inserted in the sulcus of the lower first molar for measuring the depth of the sulcus;

FIG. 8 illustrates the probe blade on the mesiobuccal side of the tooth;

FIG. 9 illustrates the probe blade rotated to facilitate the measurement of the distobuccal surface;

FIG. 10 shows the blade of the probe rotated to measure the sulcus at the distal side of the tooth;

FIG. 11 shows the probe blade parallel to the lingual surface of the tooth;

DESCRIPTION OF THE INVENTION

Figure 12:
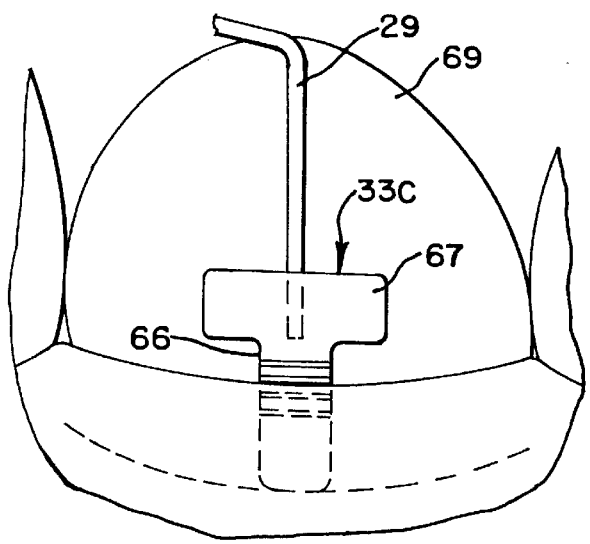
FIG. 12 is a buccal elevational view of a tooth showing a modified probe head according to the present invention having a T-shaped head with a broader portion engaging the tooth.

Referring now to the drawings, the periodontal probe of the present invention is generally indicated by the numeral 20 as shown in the FIG. 1 embodiment and includes a handle 21, a supporting arm or tip 22 extending from one end of the handle, and a head 23 rotatably carried on the supporting arm 22. It will be appreciated that the handle and tip may be made from any suitable autoclavable stainless steel, although other suitable materials could also be used. Further, the head 23 is permanently rotatably attached to the supporting arm 22 in this embodiment, although it will be appreciated that in later embodiments to be described, the head may be made of a suitable plastic and which may be removably attached to the supporting arm of the probe, and therefore disposable. In that event, only the handle need be sterilized or autoclaved, as new heads would be used for each patient.

The probe handle 21 may include a knurled section 25 at the forward end to facilitate grasping of the handle, and the handle tapers down to the supporting arm or tip 22 which is suitably held by the handle. The tip 22 includes a straight section 27 extending axially from the handle. At the outer end of the section 27 a section 28 connects the section 27 to a stem 29 that extends at an angle to facilitate the ergonomic use of the probe. The rotatable head 23 is suitably attached to the stem 29.

While it may be appreciated that the head 23 may be suitably connected for rotation on the stem 29 in this embodiment, the head 23 includes a sleeve portion 32 received on the stem 29 of the tip 22. A blade-shaped or paddle-shaped portion 33 extends from the sleeve portion 32. As seen in FIG. 5, the stem 29 is telescopically received within the tube-shaped portion 32. In order to maintain the head 23 on the stem 29, the stem is provided with an annular groove 35 and the sleeve 32 is crimped to provide a crimped portion 36 extending into the groove in order to lock the head onto the stem of the tip while allowing free rotation. It will be appreciated that the crimped or indented portion 36 engages in the stem groove to retain the head on the handle and enable the head to freely rotate on the handle stem 29. Thus, the head 23 is rotatably carried on the end of the handle 21.

As seen in FIGS. 2, 3, and 6, the blade-shaped head 33 includes opposed substantially parallel extending faces 38 and 39 interconnected by opposed edges 40 and 41 and which collectively terminate in a substantially thin end 42. While the blade shaped portion 33 may be of any suitable dimension, the distance between the very tip end 42 and the junction between the blade portion 33 and the sleeve portion 32 may be about eight to nine millimeters, about 0.060 inches in width between the edges 40 and 41 and no more than 0.015 inch in thickness between the parallel faces 38 and 39. Actually, the thickness can be less than 0.015 inch, thereby providing greater patient comfort. Additionally, measurement indicia in the form of lines or markings 44 may be provided along one or both of the faces 38 and 39 wherein the lowermost marking would be about three millimeters above the tip end 42 and the dimension between the top and bottom line would be about two millimeters. Thus, insertion of the blade head into the sulcus and lightly engaging the bottom would enable a dentist to view the indicia and determine the depth of the sulcus.

As seen in FIG. 7, a tooth 46 is shown against one side of which is illustrated the gingival or gum 48 having a free gum margin 49. Between the gum and the tooth surface a sulcus 50 is defined which is along that part of the gum that is not attached to the tooth. At the base of the gingival sulcus, periodontal fibers 51 attach the gingiva to the tooth. Thus, the gingival pockets or sulcus comprise that part of the unattached gingiva, and it is the depth of these pockets that is measured in order to evaluate gum health.

Figure 17:
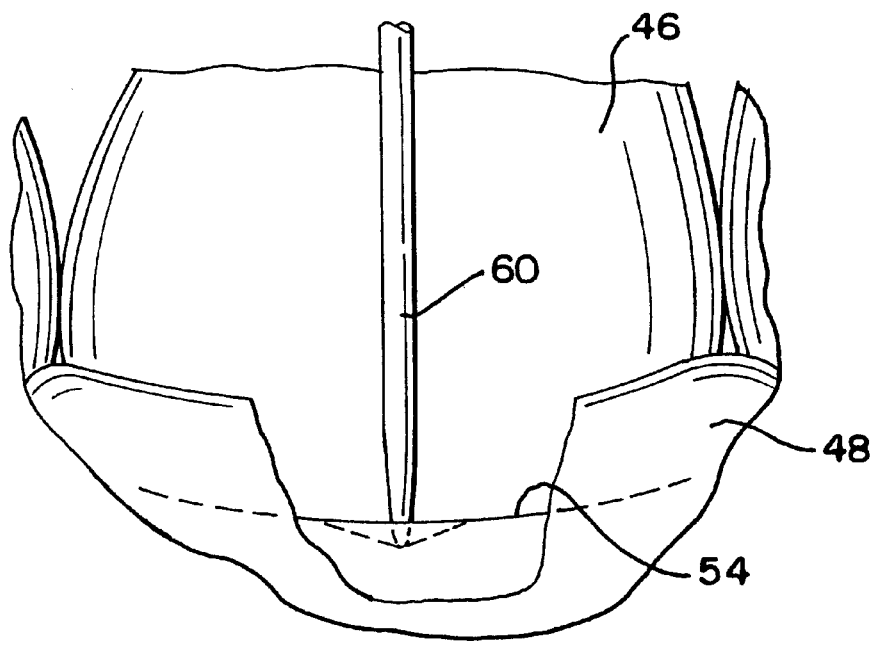
FIG. 17 is a labial view of a fragmentary tooth with the gum broken away to show the bottom of the sulcus and to illustrate how the prior art probe engages a small area and which might penetrate the periodontal fibers.

It will be appreciated that the edges and corners of the blade-shaped head 33 will be slightly rounded or smooth so as to minimize any sharp edges that could contact the gingiva of a patient. Heretofore known probes are on the order of 0.015 inch in diameter, as seen in FIG. 17, and which engage a very small area at the bottom of the sulcus. It will be appreciated that the width of the blade-shaped head of the present invention may be on the order of four times greater than the diameter of known probes. As particularly shown in FIG. 17, a tooth 46 is illustrated with the gum or gingiva 48 partially broken away. The line 54 represents the bottom of the gingival pocket, and the prior art needle-like probe is shown, as indicated by the numeral 60. It is illustrated as depressing and penetrating the periodontal fibers by extending below the bottom 54 of the sulcus. The relatively broad headed probe of the present invention provides a broad surface against the bottom of the pocket and the periodontal fibers in order to generally prevent such penetration of the fibers.

In operation, the probe of the above embodiment is shown in FIGS. 8 to 11 positioned in the sulcus of a lower right first molar 62 to measure depth. As shown in FIG. 8, the probe of the present invention is measuring the depth of the gingival sulcus on the mesiobuccal surface of the molar, while in FIG. 9, after removing the probe from the sulcus, and inserting it at another location, the probe is measuring the distobuccal surface of the molar. The blade rotates on the handle as it moves along the outer surface of the tooth. Again, the head has rotated as shown in FIG. 10 to measure the sulcus at the distal surface of the molar, while in FIG. 11, the head of the probe of the present invention has again rotated to measure the sulcus at the lingual surface of the molar. Thus, as the probe moves around the tooth to measure sulcus depth at another location, the head rotates along the surface of the tooth, and inasmuch as the surface is substantially flat, the rotation is driven by engagement between the blade of the probe and the surface of the tooth. Thus, the measurement process is facilitated and made much easier to be completed by the dentist, while at the same time the comfort of the patient is assured inasmuch as there will not be any penetration or puncturing of the periodontal fibers at the base of the sulcus. The flat side of the blade accordingly parallels the surface of the tooth during the measurement process. The dentist or hygienist need not rotate the handle of the probe to achieve the parallelism. Rather, the user need only place the blade in contact with the surface of the tooth.

Although the opposite surfaces of the bladed head are parallel in the embodiment of FIGS. 1 to 3 and 5 to 11, these surfaces could be tapered, as illustrated in FIG. 4 with the thinnest edge being the lead edge as the probe is moved around the tooth. The embodiment of FIG. 4 is generally indicated by the numeral 33A and which only differs from the embodiment in FIGS. 2 and 3 in that the opposite broad faces 38a and 39a are non-parallel and as looking at the transverse cross section the shape defines a tapered blade. It will be appreciated that any suitable blade or paddle-shaped configuration may be provided as long as it is not too thick to fit in the sulcus and will serve to rotate on the end of the handle of the probe.

Figure 13:
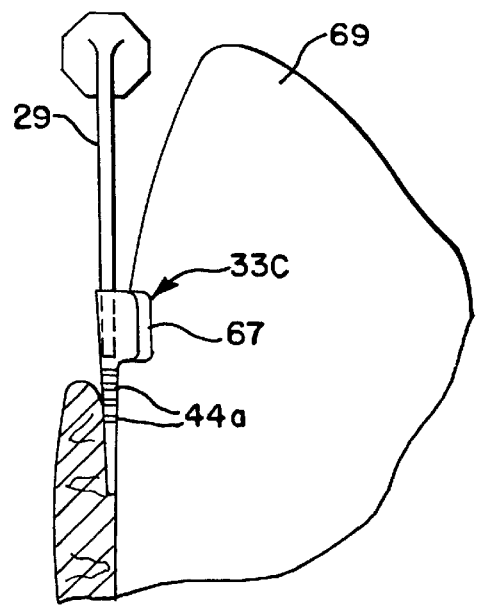
FIG. 13 is an end elevational view of the probe head of FIG. 12 and illustrating that the upper end of the probe head can be curved to better engage the surface of a tooth.

Another embodiment of the invention is shown in FIGS. 12 and 13, wherein the blade-shaped head, generally designated by the numeral 33C, is T-shaped as looking at it from the labial and wherein the bladed head includes a lower vertical section or portion 66 and an upper horizontally extending portion 67 which provides a broader engagement of the outer surface of the tooth above the gum margin. The width of the lower section would be similar to the width of the bladed head 33. Also, the thickness would be about the same, but the width of the upper section 67 would be much broader in order to provide a greater surface contact during traversing the surface of a tooth. Additionally, as seen in FIG. 13, the upper horizontal section 67 can be arcuately formed to substantially mate with the outer arcuate surface of the tooth. The head 33C of this embodiment is also rotatably mounted on the stem 29 so that it will rotate as it is moved between measuring locations around the tooth. It is illustrated in FIG. 12 against the outer or labial side of the tooth 69, while in both FIGS. 12 and 13, it is illustrated as being inserted in the sulcus of the tooth in order to measure the depth of the sulcus. Again, scaled lines or markings 44a are provided on the exterior surface of the head in order to facilitate measuring the depth of the sulcus. This head could also be triangularly shaped to provide a relatively broad upper section and narrow gingival section. It should also be appreciated that the head may be oval or of any shape that would include a broad tip for engaging along the periodontal fibers at the bottom of the sulcus.

Figure 14:
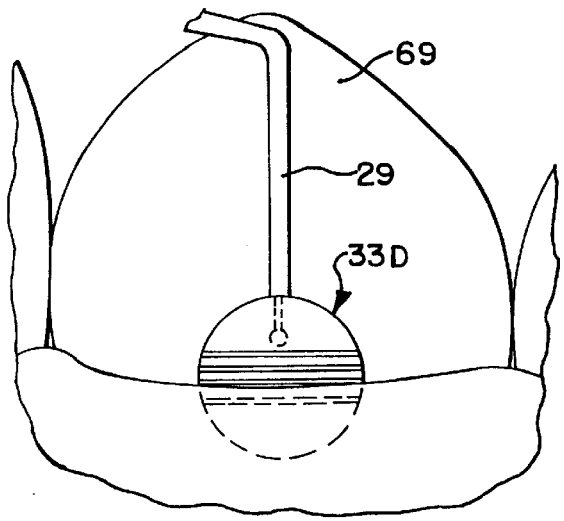
FIG. 14 is a view like FIG. 12 but illustrating a further embodiment of the invention wherein the probe head is in the form of a disc.
Figure 15:
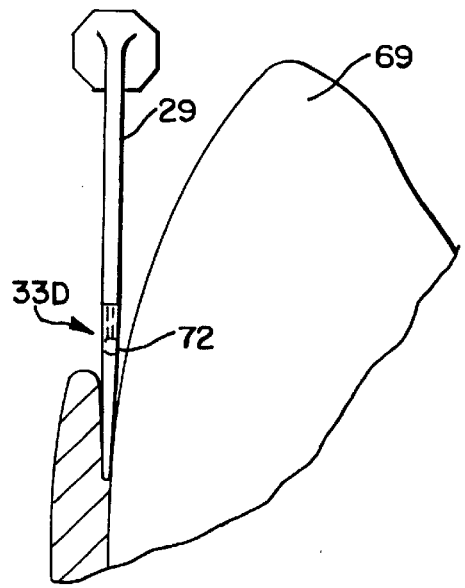
FIG. 15 is an end elevational view like FIG. 13 of the embodiment of FIG. 14 to show how the disc-shaped head engages in the sulcus of a tooth.

Another embodiment of the invention is shown in FIGS. 14 and 15, wherein the blade-shaped head indicated as 33D is disc-shaped and removably mounted on the lower end of the handle stem 29. The lower end of the handle stem 29 is provided with a ball-shaped end 72 so that the disc-shaped head 33D, may be removably connected to the handle, as will be more particularly explained below in connection with the embodiment of FIG. 16. The disc-shaped head is shown in the sulcus of both FIGS. 14 and 15 for the purpose of measuring the depth of the gingival pocket. Again, several markings or indicia are provided on at least one or both faces of the disc-shaped head in order to assist in the measurement of the depth of the sulcus. This particular disc-shaped head may be molded from a suitable plastic, whereby it may be removable from the stem and disposable at the end of its use for a particular patient. This facilitates the sterilizing of the handle inasmuch as it will be a one-piece structure. Again, the disc-shaped head would be carried rotatably by the handle such that it can easily traverse a tooth surface and rotate on the handle as it is moved around a tooth.

Figure 16:
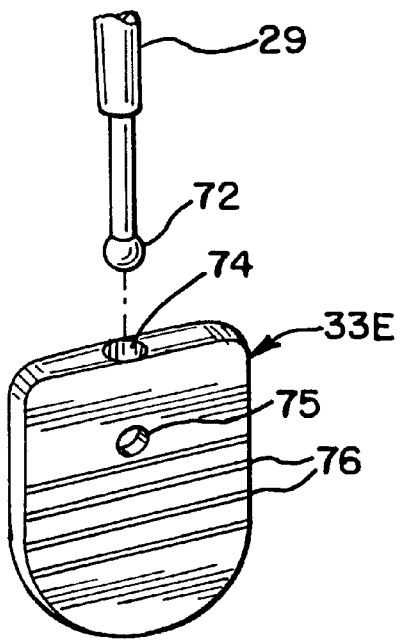
FIG. 16 is an exploded perspective view of a modified head and handle stem similar to the disc-shaped head of FIGS. 14 and 15 and illustrating how the head may be easily removed or placed on the end of the handle.

A further embodiment of the invention is shown in FIG. 16, which differs from the embodiment of FIGS. 14 and 15 only in that the blade-shaped head 33E is elongated in configuration rather than disc-shaped. Further, the ball-shaped end 72 of the stem 29 is shown in exploded position from the head 33E. The head 33E includes a bore 74 which extends into the upper end of the head and terminates at apertures 75 at both sides of the head, and accordingly, insertion of the ball-shaped end into the opening of the head is completed when the head reaches the area of the opposed openings or apertures 75 and then snaps in place. Thus, a snap-fit is established between the head and the handle. This will provide a rotatable connection between the head and stem handle so that the head can rotate as necessary to measure sulcii depths at various locations around a tooth. Markings or indicia 76 are provided along at least one side of the head to facilitate the measurement of the depth of the sulcus.

In view of the foregoing, it may be appreciated that the present invention has a rotatable head on a probe which facilitates the examination of the depth of the sulcus in a patient's mouth about a particular tooth. The head of the probe is provided with a blunt end or broad surface in order to make the examination more comfortable to the patient and also to avoid possible puncture of the periodontal fibers at the base of the sulcus.

It will be understood that modifications and variations may be effected without departing from the scope of the novel concepts of the present invention, but it is understood that this application is to be limited only by the scope of the appended claims.

The invention is hereby claimed as follows:

1. A periodontal probe for measuring the depth of the gingival sulcus of a patient's teeth by insertion into and/or traversing of the gingival sulcus, said probe comprising:
   a handle, and
   a head at one end of the handle rotatably mounted on the handle.

2. The probe of claim 1, wherein the head is blade-shaped and includes opposed substantially flat sides.

3. The probe of claim 2, wherein the head extends at an angle to the handle.

4. The probe of claim 3, wherein the opposite sides of the head are substantially parallel to each other.

5. The probe of claim 3, wherein the opposite sides of the head are non-parallel to each other.

6. The probe of claim 2, wherein the head further includes measurement indicia on at least one side.

7. The probe of claim 2, wherein the very end of the head is thin and broad.

8. The probe of claim 2, wherein the head is removably connected to the handle.

9. The probe of claim 2, wherein the opposite sides of the head are tapered.

10. The probe of claim 2, wherein the head is removable and disposable.

11. The probe of claim 1, wherein the head is substantially disc shaped.

12. The probe of claim 1, wherein the head is substantially square shaped.

13. The probe of claim 1, wherein the head is snap-fitted to the handle and disposable.

14. The probe of claim 13, wherein the head extends at an angle to the handle and includes opposed substantially flat sides and a substantially thin end.

15. The probe of claim 14, wherein the head is plastic.

16. The probe of claim 1, wherein the head is paddle-shaped.

17. The probe of claim 1, wherein the head is T-shaped.

18. The probe of claim 17, wherein the head includes a vertical paddle-shaped portion and a horizontal arcuately shaped portion.

19. The probe of claim 18, wherein markings are provided on the paddle-shaped portion for measuring the depth of the sulcus.

20. The probe of claim 1, wherein the head is triangularly shaped.

21. A periodontal probe for measuring the depth of the gingival sulcus of a patient's teeth by insertion into and/or traversing of the gingival sulcus, said probe comprising:
   a handle,
   a stem at one end of the handle extending angularly to the handle,
   a ball end on the stem, and
   a head snap-fitted on the ball end having a substantially blade-shaped configuration.

22. The probe of claim 21, wherein the head is substantially circular in shape.

23. The probe of claim 21, wherein the head is substantially rectangular in shape.

24. The probe of claim 21, wherein the head is substantially oval in shape.

25. The probe of claim 21, wherein the handle and stem are of stainless steel and the head is of plastic and disposable.

26. The method of measuring the depth of the gingival sulcus of a tooth with an instrument having a handle and a rotating substantially flat sided thin head having a broad end and indicia thereon, comprising the steps of:
   inserting the head of the instrument between the gingiva and the outer or crown surface of the tooth with one of the sides against the tooth until the broad end hits the bottom of the sulcus, and
   visually reading the indicia.

27. The method of claim 26, which further includes the step of intermittently moving the head from one location to other locations for measuring the sulcus depth at said other locations.

* * * * *

UNITED STATES PATENT AND TRADEMARK OFFICE
CERTIFICATE OF CORRECTION

PATENT NO. : 6,024,564   Page 1 of 1
DATED : February 15, 2000
INVENTOR(S) : Peter C. Kesling It is certified that error appears in the above-identified patent and that said Letters Patent is hereby corrected as shown below:

Title page,
ABSTRACT, line 1, after "having" insert -- a rotating --;

Column 6,
Lines 36-37, change to read -- gingival sulcus around a patient's tooth, said probe comprising: --;
Line 39, before "head" insert -- blade-shaped -- and delete "at one end of the handle";
Line 41, before "head" insert -- blade-shaped -- and delete "is blade-shaped";
Line 42, delete "and";

Column 7,
Lines 14-15, change to read: -- gingival sulcus around a patient's tooth, said probe comprising: --.

Signed and Sealed this

Fifth Day of February, 2002

*Attest:*

JAMES E. ROGAN
*Attesting Officer*   *Director of the United States Patent and Trademark Office*